United States Patent [19]

Rothschild et al.

[11] Patent Number: 5,935,784
[45] Date of Patent: Aug. 10, 1999

[54] PROLACTIN RECEPTOR GENE AS A GENETIC MARKER FOR INCREASED LITTER SIZE IN PIGS

[75] Inventors: Max F. Rothschild, Ames; Amy L. Vincent, Jewell; Christopher K. Tuggle, Ames, all of Iowa

[73] Assignee: Iowa State University Research Foundation, Inc., Ames, Iowa

[21] Appl. No.: 08/812,208

[22] Filed: Mar. 6, 1997

Related U.S. Application Data

[63] Continuation of application No. 08/742,805, Nov. 1, 1996, abandoned

[60] Provisional application No. 60/022,180, Jul. 19, 1996.

[51] Int. Cl.[6] .............................. C12Q 1/68; C12P 19/34; C07H 21/02; C07H 21/04
[52] U.S. Cl. .............................. 435/6; 435/18; 435/91.2; 435/91.21; 536/23.1; 536/24.3; 536/24.31; 536/24.32; 536/24.1; 536/24.2; 536/24.33
[58] Field of Search .................................. 536/23.1, 24.3, 536/24.31, 24.32, 24.33, 24.1, 24.2; 435/6.18, 91.2, 91.21, 810

[56] References Cited

U.S. PATENT DOCUMENTS 5,374,526 12/1994 Rothschild et al. ......................... 435/6
5,550,024 8/1996 Rothschild et al. ......................... 435/6

FOREIGN PATENT DOCUMENTS

WO 96/33288 10/1996 WIPO .............................. C12Q 1/68
WO 96/41892 12/1996 WIPO .............................. C12Q 1/68

OTHER PUBLICATIONS

Stratagene Catalog, pp. 131 and 161, 1995.
Edery et al, "Identification and sequence analysis of a second form of prolactin receptor by molecular cloning of complementary DNA from rabbit mammary gland", Proc. Natl. Acad. Sci. 89:2112–2116, Mar. 1989.
Sommers et al, "minimal homology requirements for PCR primers", Nucleic Acids Res. 17(16):6749, 1989.
Rothschild, et al., "The estrogen receptor locus is associated with a major gene influencing litter size in pigs", *Proc. Natl. Acad. Sci. USA* 93:201–205 (1996).

Primary Examiner—Jeffrey Fredman
Attorney, Agent, or Firm—Zarley, McKee, Thomte, Voorhees & Sease

[57] ABSTRACT

Disclosed herein are genetic markers for pig litter size, methods for identifying such markers, and methods of screening pigs to determine those more likely to produce larger litters and preferably selecting those pigs for future breeding purposes. The markers are based upon the presence or absence of certain polymorphisms in the pig prolactin receptor gene.

3 Claims, 2 Drawing Sheets

AAGTCAACAA AGATGGAGCA CTGGCGTTGC TCCCAAAACA GCAGGAGAAC

GGCGACCGGC CGGAGAAGGC TGGCGCCCCT GAAACCAGCA AGGAATACG

CCCAGGTGTC CCGGGTGATG GATAACCACA TCCTGGTGTT AGTGCAGGAT

CCGCGAGCTC GAAACGTGGC TCCGTTTGAA GAACCAACCA AGGAGACCCC

GCCATCCCGG CCGCAGAATC CAGCTGCGAA AGACCTGGCC G/AGCTTCACCA

CGGCCCCGGG CCACTGCAGA CACCCGCTGG GTGGGCTGGA TTACCTCGAT

CCCGCAGGCT TTATGCACTC CTTTCAGTGA GAGCTTGGTT CATGGGATGA

TGGGTTACAA GGTGGGGTTT TTTTCAGGTC GCACTACGTG AAATGCACTC

TACCAGAGAA AGCTCGAAAA TGGGGTTAGA ATGACACTAC *CCAGACTCAC*

*AGTTCACTCC TCTTCATGCT* CCATTTTCAA CCACTTGCCTCTT

G/A=G or A at polymorphic site

*Fig.1*

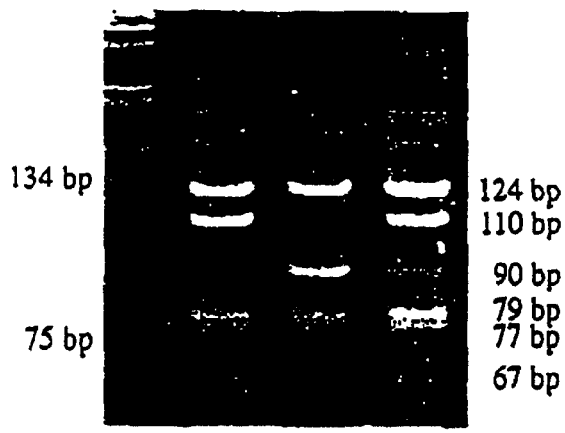

*Fig.2*

PROLACTIN RECEPTOR GENE AS A GENETIC MARKER FOR INCREASED LITTER SIZE IN PIGS

CROSS REFERENCE TO RELATED APPLICATION

This application is a continuation of commonly owned U.S. patent application Ser. No. 08/742,805 filed Nov. 1 1996, now abandoned, which is a continuation of commonly owned United States provisional application Ser. No. 60/022,180 filed Jul. 19, 1996, now abandoned, entitled DNA POLYMORPHISMS IN GENES THAT ARE USEFUL FOR TESTING AND SELECTING FOR INCREASED LITTER SIZE IN PIGS, priority is claimed under 35 U.S.C. Section 120.

FIELD OF THE INVENTION

This invention relates generally to the detection of genetic differences for reproductive efficiency among pigs and particularly use of a genetic marker prolactin receptor gene which is indicative of the heritable trait of increased litter size.

BACKGROUND OF THE INVENTION

Reproductive efficiency, which can be defined as the number of pigs produced per breeding female, is the major limiting factor in the efficient production of pork. The number of pigs born alive in the United States averages approximately 9.5 pigs per litter. Heritability for litter size is low (10%–15%), and standard genetic methods of selecting breeding females on the basis of past litter size have not been effective. Therefore, there is a need for an approach that deals with selection for reproduction at the cellular or DNA level.

Chinese breeds are known for reaching puberty at an early age and for their large litter size. American breeds are known for their greater growth rates and leanness. Thus, it would be desirable to combine the best characteristics of both types of breeds, thereby improving the efficiency of U.S. pork production. These efforts would be greatly assisted by the discovery of genes or genetic markers that are associated with increased litter size in pigs.

RFLP analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., Abstract for Annual Meeting of Midwestern Section of the American Society of Animal Science, Mar. 26–28, 1990, incorporated herein by reference, reports on the polymorphism of swine major histocompatibility complex (MHC) genes for Chinese pigs, also demonstrated by RFLP analysis. Jung et al. *Animal Genetics*, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

Further, U.S. Pat. No. 5,550,024 to Rothschild et. discloses a polymorphism in the pig estrogen receptor gene which is associated with larger litter size, the disclosure of which is incorporated herein by reference.

Another pig hormone related to reproductive success is Prolactin. Prolactin (PRL) is an anterior pituitary peptide hormone involved in many different endocrine activities, but is essential for reproductive success. One of its best characterized functions is regulating milk production in adult mammals. PRL is required for the stimulation of lactogenesis, or synthesis of milk proteins. This action is mediated by its receptor (PRLR). PRLR belongs to the cytokine/GHR/PRLR superfamily. When activated by PRL, PRLR begins a signal transduction pathway, which ultimately activates transcription of genes such as β-casein and α-lactalbumin. When activated by PRL, PRLR begins a signal transduction pathway thought to involve the tyrosine kinase Jak2. Mutations in the carboxy-terminal end of the protein which change a specific phosphotyrosine residue prevents the receptor from activating Jak2 and ultimately interferes with the activation of transcription of the β-casein gene (Lebrun). Long and short forms of the receptor protein, as well as various transcript sizes have been characterized in the rat, mouse, rabbit, and human. (Boutin, Edery, Lesueur). However, it has been demonstrated that the short form is not capable of activating transcription of the milk protein genes. The mRNAs seen thus far originate from the same primary transcript and are due to alternative splicing, specifically in the untranslated regions in the rabbit and human. Recently, PRL has also been shown to stimulate the production of progesterone, required for maintenance of pregnancy, in large porcine luteal cells in vitro. PRLR is thought to mediate the effects of growth hormone (bST) injections on higher milk yield in cattle, and thus may be important in varying milk yield in pigs. In humans and mice, the growth hormone receptor (GHR) and PRLR map close together (Arden et al., 1990; Barker et al., 1992), making it likely that these two genes are linked in pigs. GHR has been mapped in pigs to chromosome 16, while PRLR is unmapped and no genetic variability has been reported for PRLR.

The present invention provides a genetic marker, based upon the discovery of polymorphisms in the prolactin receptor gene, which relates to increased average litter size in pigs. This will permit genetic typing of pigs for their prolactin receptor genes and for determination of the relationship of specific RFLPs to increased litter size. It will also permit the identification of individual males and females that carry the gene for larger litters. In the case of females it would permit that a female would be expected to produce a litter size larger than the average for their breed, or in the case of males for their female offspring to have larger litters than the breed average. Thus, the markers will be selection tools in breeding programs to develop lines and breeds that produce litters containing a larger number of offspring.

SUMMARY OF THE INVENTION

It is an object of the invention to provide a method of screening pigs to determine those more likely to produce larger litters.

Another object of the invention is to provide a method for identifying genetic markers for pig litter size.

A further object of the invention is to provide genetic markers for pig litter size.

Yet another object of the invention is to provide a kit for evaluating a sample of pig DNA for specific genetic markers of litter size.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

To achieve the objects and in accordance with the purpose of the invention, as embodied and broadly described herein, the present invention provides a method for screening pigs to determine those more likely to produce a larger litter when bred or to select against pigs which have alleles indicating smaller litter sizes. As used herein "larger litters" means a significant increase in litter size above the mean of a given population. Thus, the present invention provides a method for screening pigs to determine those more likely to produce larger litters, and/or those less likely to produce larger litters, which method comprises the steps 1) obtaining a sample of genomic DNA from a pig; and 2) analyzing the genomic DNA obtained in 1) to determine which prolactin allele(s) is/are present. Briefly, a sample of genetic material is obtained from a pig, and the sample is analyzed to determine the presence or absence of a polymorphism in the prolactin receptor gene that is correlated with increased litter size.

In a preferred embodiment the polymorphism is a restriction fragment length polymorphism and the assay comprises identifying the pig prolactin receptor gene from isolated pig genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a pig prolactin receptor gene that is either known to have or not to have the desired marker. If a pig tests positive for the marker, such pig can be considered for inclusion in the breeding program. If the pig does not test positive for the marker genotype the pig can be culled from the group and otherwise used.

In a most preferred embodiment the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying a genetic marker for pig litter size in a particular population. Male and female pigs of the same breed or breed cross or similar genetic lineage are bred, and the number of offspring produced by each female pig is determined. A polymorphism in the prolactin receptor gene of each pig is identified and associated with the number of offspring. Preferably, RFLP analysis is used to determine the polymorphism, and most preferably, the DNA is digested with the restriction endonuclease AluI.

It is also possible to establish linkage between specific alleles of alternative DNA markers and alleles of DNA markers known to be associated with a particular gene (e.g. the prolactin receptor gene discussed herein), which have previously been shown to be associated with a particular trait. Thus, in the present situation, taking the prolactin receptor gene, it would be possible, at least in the short term, to select for pigs likely to produce larger litters, or alternatively against pigs likely to produce smaller litters, indirectly, by selecting for certain alleles of a prolactin receptor associated marker through the selection of specific alleles of alternative chromosome 16 markers. Examples of such markers known to be linked to prolactin receptor on porcine chromosome 16 includes SW1305, S0077, S0006, SW2411, SW1035 and S0111, which markers are all microsatellites and Growth Hormone Receptor (GHR).

The invention further comprises a kit for evaluating a sample of pig DNA for the presence in pig genetic material of a desired genetic marker located in the pig prolactin receptor gene indicative of the inheritable trait of large litter size. At a minimum, the kit is a container with one or more reagents that identify a polymorphism in the pig prolactin receptor gene. Preferably, the reagent is a set of oligonucleotide primers capable of amplifying a fragment of the pig prolactin receptor gene that contains the polymorphism. Preferably, the kit further contains a restriction enzyme that cleaves the pig prolactin receptor gene in at least one place. In a most preferred embodiment the restriction enzyme is AluI or one which cuts at the same recognition site.

The accompanying figures, which are incorporated herein and which constitute a part of this specification, illustrates one embodiment of the invention and, together with the description, serve to explain the principles of the invention.

DESCRIPTION OF THE FIGURES

FIG. 1 depicts the sequence of the 3' coding and untranslated region of the pig prolactin receptor gene (SEQ ID NO:3). The pig PCR fragment produced from the rabbit/human primers was purified using Amicon Microcon Filters as directed (Amicon, Inc.). Sequencing was done by the Iowa State University DNA Sequencing and Synthesis Facility. Region in italics represents ambiguity in sequence and may be ccaaaactac (SEQ ID NO:3) ΔPig PCR primers.–Rabbit/human sequence.

FIG. 2 depicts the Polymorphic pattern of AluI digested PCR product. The forward primer 5'-CCC AAA ACA GCA GGA GAA CG-3' and the reverse primer 5'-GGC AAG TGG TTG AAA ATG GA-3' were used in the following PCR conditions: 93° C. for 3 minutes, and 35 cycles of 93° C. 30 seconds, 60° C. 1 minute, 70° C. 1 minute, and a final 72° C. 3 minutes. The Taq Polymerase was added last while samples were held at 80° C. PCR products were cut with Alu I (New England Biolabs) and separated on a 6% NuSieve (FMC) agarose gel at 120 volts for 4 hours at room temperature. Gels were stained with ethidium bromide. Lane 1 is 1-kb ladder, lanes 2–4 are the three different genotypes.

DETAILED DESCRIPTION OF THE INVENTION

Figure 3:
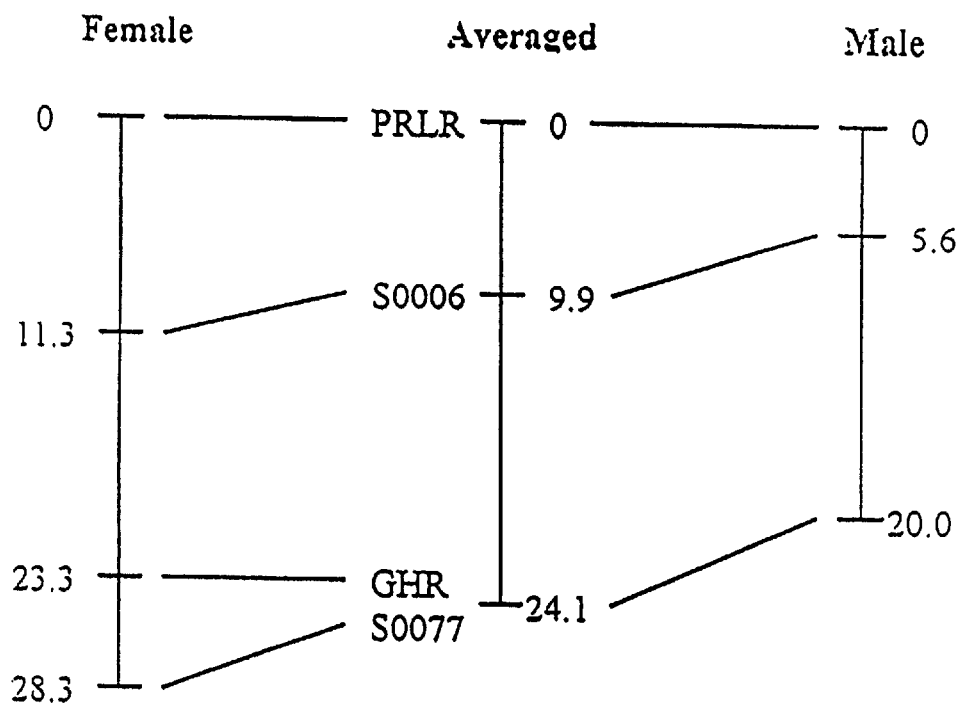
FIG. 3 depicts the position of PRLR in pig chr 16. Multiple point linkage was done using CriMap to produce a sex-averaged best-map with a LOD score of 3 or greater being considered as significant.

Reference will now be made in detail to the presently referred embodiments of the invention, which together with the following examples, serve to explain the principles of the invention.

The invention relates to genetic markers for litter size in pigs. It provides a method of screening pigs to determine those more likely to produce a larger litter when bred by identifying the presence or absence of a polymorphism in the prolactin receptor gene that is correlated with increased litter size. As used herein, the term "increased litter size" means a biologically significant increase in litter size above the mean of a given population.

Thus, the invention relates to genetic markers and methods of identifying those markers in a pig of a particular breed, strain, population, or group, whereby the female pig is more likely to produce a litter that is significantly increased in size (number) above the mean litter size for that particular breed, strain, population, or group. Any method of identifying the presence or absence of this marker may be used, including for example single-strand conformation polymorphism (SSCP) analysis, RFLP analysis, heteroduplex analysis, denaturing gradient gel electrophoresis, and temperature gradient electrophoresis, ligase chain reaction or even direct sequencing of the prolactin receptor gene and examination for the AluI recognition pattern, in the 3' translated and nontranslated region.

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

The use of RFLPs is the preferred method of detecting the polymorphism. However, since the use of RFLP analysis depends ultimately on polymorphisms and DNA restriction sites along the nucleic acid molecule, other methods of detecting the polymorphism can also be used. Such methods include ones that analyze the polymorphic gene product and detect polymorphisms by detecting the resulting differences in the gene product.

RFLP analysis in general is a technique well-known to those skilled in the art. See, for example, U.S. Pat. Nos. 4,582,788 issued Apr. 15, 1986 to Erlich and 4,666,828 issued May 19, 1987 to Gusella, 4,772,549 issued Sep. 20, 1988 to Frossard, and 4,861,708 issued Aug. 29, 1989 to Frossard, all of which are incorporated herein by reference. Broadly speaking, the technique involves obtaining the DNA to be studied, digesting the DNA with restriction endonucleases, separating the resulting fragments, and detecting the fragments of various genes.

In the present invention, a sample of genetic material is obtained from a pig. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Next the region containing the polymorphism is amplified by the use of primers and standard techniques, such as the polymerase chain reaction. This technique is described in U.S. Pat. Nos. 4,683,195, issued Jul. 28, 1987 to Mullis et al., 4,683,202, issued Jul. 28, 1987 to Mullis, 4,800,159 issued Jan. 24, 1989 to Mullis, et al., 4,889,818 issued Dec. 26, 1989 to Gelfand, et al., and 4,902,624, issued Feb. 20, 1990 to Clumbus, et al., all of which are incorporated herein by reference. The selection of primers is discussed in the references mentioned and incorporated herein. The primers should amplify the 3' coding region and untranslated and nontranslated region of the pig prolactin receptor gene as is demonstrated in FIG. 2. Other such primers are designable by those of skill in the art combined with the teachings herein.

The isolated DNA is then digested with a restriction endonuclease that cleaves or cuts DNA hydrolytically at a specific nucleotide sequence, called a restriction site. Such endonucleases, also called restriction enzymes, are well-known to those skilled in the art. For the present invention, one should be chosen that cleaves the pig prolactin receptor gene in at least one place, producing at least two fragments of the gene. A determination is made as to whether or not any such fragments are polymorphic and if any polymorphism (RFLP) is associated with litter size by techniques known in the art in conjunction with the teachings contained herein. Preferably, the restriction endonuclease is AluI. AluI cuts double stranded DNA at the sequence 5'-AGCT-3'. The amount of such enzyme to be added to the sample containing the pig DNA and the other appropriate conditions for treating the sample will be readily determinable to persons skilled in the art, given the teachings contained herein.

The restriction fragments are then analyzed by known techniques that generally involve either the separation of the fragments and visualization by staining or subsequent blotting and hybridization to obtain a particular pattern or the determination of different sizes of the fragments. The latter permits the identification of one or more fragments (markers) for increased litter size. The preferred separation technique is gel electrophoresis.

In this technique, the digested fragments are separated in a supporting medium by size under the influence of an applied electric field. Gel sheets or slabs, such as agarose or agarose-acrylamide, are typically used as the supporting medium. The sample, which contains the restriction fragments, is added to one end of the gel. One or more size markers are run on the same gel as controls to permit an estimation of the size of the restriction fragments. This procedure generally permits a degree of resolution that separates fragments that differ in size from one another by as little as 100 base pairs.

In alternative embodiments, the fragments are denatured and transferred physically from the gel onto a solid support, preferably a nylon membrane, by contacting the gel with the filter in the presence of appropriate reagents and under appropriate conditions that promote the transfer of the DNA. Such reagents and conditions are well-known to those skilled in the art. Thus, the relative positions of the DNA fragments resulting from the separation procedure are maintained.

The next step involves the detection of the various categories of sizes of the fragments or, alternatively, the detection of a fragment of a particular size. The latter may be of particular interest because it is a genetic marker associated with increased litter size. This is preferably accomplished via staining of the fragments with ethidium bromide or the like.

An alternative technique is the use of a hybridization probe. Such a probe is an oligonucleotide or polynucleotide that is sufficiently complementary or homologous to the fragments to hybridize with them, forming probe-fragment complexes. Preferably, the probe is a cDNA probe. The oligonucleotide or polynucleotide is labeled with a detectable entity. This permits the detection of the restriction fragments, to which the probes are hybridized. The probes are labeled by standard labeling techniques, such as with a radiolabel, enzyme label, fluorescent label, biotin-avidin label, and the like. See U.S. Pat. Nos. 4,711,955 issued Dec. 8, 1987 to Ward et al. and 4,868,103 issued Sep. 19, 1989 to Stavrianopoulos et al., both of which are incorporated herein by reference.

The probes are contacted with the nylon membrane that contains the restriction fragments for a sufficient period of time and under appropriate hybridizing conditions for the probes to hybridize to the fragments. The filter is then preferably washed to remove unbound probes and other unwanted materials.

The probe-fragment complexes, which are bound to the filter, are then detected by known techniques. For example, if the probe has been radioactively labeled ($^{32}$p), detection involves contacting the nylon membrane paper with a piece of radiosensitive film. Following an appropriate exposure period, the fragments of interest, including control fragments, are visualized.

The detection step provides a pattern, resulting from the separation of the fragments by size. Comparison of these fragments with control fragments of known size that have also been run on the same gel permits the estimation of the size of the various groups of fragments. The various polymorphisms in the pig prolactin receptor gene are then determined by comparison of the patterns produced by similar analysis of DNA from a number of different pigs. For some of the individual pigs, the patterns will differ from the usual pattern produced by most of the other pigs. This will be due to one or more restriction fragment length polymorphisms, i.e., restriction fragments of a different length produced by the endonuclease that cuts the pig prolactin receptor gene. This indicates different base pair sequences in such pigs.

Once a particular RFLP has been identified, i.e., a restriction fragment of a particular length, a probe to this fragment may be constructed by the use of known techniques. This permits alternative and faster formats for detecting such polymorphism. For example, once the DNA is digested, a sandwich hybridization format can be used. Such an assay is disclosed in U.S. Pat. Nos. 4,486,539 issued Dec. 4, 1984 to Ranki, et al., and 4,563,419 issued Jan. 7, 1986 to Ranki, et al., both of which are incorporated herein by reference. The sample is brought into contact with a capture probe that is immobilized on a solid carrier. The probe binds the fraggment. The carrier is then washed, and a labeled detection probe is added. After additional washing, the detection probe is detected, thereby demonstrating the presence of the desired fragment.

In yet another embodiment, once the RFLP pattern has been determined or a particular polymorphic fragment has been determined, it is compared to a second, known RFLP pattern or fragment that is correlated with increased litter size. This second pattern or fragment has also been determined from the pig prolactin receptor gene, using the same restriction endonuclease as the first and the same probe or an equivalent thereof under the same conditions.

In an alternative embodiment of the invention, the restriction fragments can be detected by solution hybridization. In this technique, the fragments are first hybridized with the probe and then separated. The separated probe-fragment complexes are then detected as discussed above. Generally, such complexes are detected on the gel without transfer to filter paper.

In a most preferred embodiment the polymorphism is detected by PCR amplification without any probe. This procedure is known to those of skill in the art and is disclosed in U.S. Pat. Nos. 4,795,699 entitled "DNA Polymerase" and U.S. Pat. No. 4,965,188 "Process for Amplifying, Detecting, and/or Cloning Nucleic Sequences Using a Thermostable Enzyme" both of which are incorporated herein by reference.

For this procedure primers are constructed to amplify the region in which the polymorphism lies. Accordingly primers which are preferably 4–30 bases are designed based upon the sequence surrounding the polymorphism including a forward 5', primer and a reverse or anti-sense primer 3' of the polymorphism. The primers need not be the exact complement, and substantially equivalent sequences are also acceptable. A DNA polymerase is then added such as Taq polymerase (many such polymerases are known and commercially available) in the presence of the four nucleoside triphosphates and often a buffering agent. Detection is facilitated by simple staining, such as with ethidium bromide, of separated products to detect for predicted sizes based upon the length of the region amplified. Reaction times, reagents, and design of primers are all known to those of skill in the art and are discussed in the patents incorporated herein by reference. Further PCR amplification may be used in combination with Single Strand Confirmation Polymorphism (SSCP). See Detection of Polymorphism, of Human DNA by Gel Electrophoresis as Single-Strand Conformation Polymorphisms, Orita et al, PNAS 86(8) Apr. 1989 (2766–70); and Lessa et al. Mol Ecol 2(2) p. 119–29 Apr 1993 "Screening Techniques for Detecting Allelic variation in DNA Sequences" which are incorporated by reference.

Although the above methods are described in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation.

Genetic markers for pig litter size are determined as follows. Male and female pigs of the same breed or breed cross or derived from similar genetic lineages are mated. The number of offspring produced by each female pig is determined. RFLP analysis of the parental DNA is conducted as discussed above in order to determine polymorphisms in the prolactin receptor gene of each pig. The polymorphisms are associated with the number of offspring. At least 20 and preferably at least 40 female pigs are used in making these determinations. The number of times each female produces a litter (i.e., the parity) is at least 1 time. Preferably, the cycle of breeding and giving birth is repeated at least 2 times and most preferably 3 times.

When this analysis is conducted and the polymorphism is determined by PCR RFLP analysis using the restriction endonuclease AluI, and amplification primers may be designed using analogous human or rabbit known prolactin sequences due to the high homology in the region surrounding the polymorphism, or may be designed using known pig prolactin gene sequence data as exemplified in FIG. 1 or even designed from sequences obtained from linkage data from closely surrounding genes. According to the invention a set of primers have been selected which amplify a 457 base pair fragment (forward primer 5'-CCC AAA ACA GCA GGA GAA CG-3' (SEQ ID NO:1) and the reverse primer 5'-GGC AAG TGG TTG AAA ATG GA-3' (SEQ ID NO:2)) after restriction polymorphic fragments of approximately 124, 110, 79, 77, and 67 base pairs are generated. The polymorphic site is located in the 110 base pair fragment. When the polymorphic cut site is present a 90 base pair fragment is produced. The polymorphic fragments were shown to be alleles, and each was shown to be associated with increased litter size for various breeds. Thus a pig which is heterozygous for the AluI fragment will exhibit a pattern of 124,110,90,79,77 and 67 A homozygote for the polymorphic cut site will exhibit a patter of 124, 90, 79,77, 67, while the other homozygote exhibits a pattern of 124, 110, 79,77,67. The genotype associated with larger litter size alternates for different breeds. This outcome is similar to the situation disclosed in U.S. Pat. No. 5,374,523 entitled "Allelic variants of Bovine Somatotropin gene: Genetic marker for Superior Milk Production in Bovine" where the inventor found an allelic polymorphism is the somatotropin gene and one allelic form was beneficial for jersey cows and the alternate form was beneficial for Holstein cows.

The reagents suitable for applying the methods of the invention may be packaged into convenient kits. The kits provide the necessary materials, packaged into suitable containers. At a minimum, the kit contains a reagent that identifies a polymorphism in the pig prolactin receptor gene that is associated with an increased litter size. Preferably, the reagent is a PCR set (a set of primers, DNA polymerase and 4 nucleoside triphosphates) that hybridize with the pig prolactin receptor gene or a fragment thereof. Preferably, the PCR set and a restriction enzyme that cleaves the pig prolactin receptor gene in at least one place are included in the kit. In a particularly preferred embodiment of the invention, the primer is SEQ ID NO:1 or SEQ ID NO:2 and the restriction enzyme is AluI. Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the prolactin receptor gene is present. Preferably, RFLP analysis is performed with respect to the pig prolactin receptor gene, and the results are compared with a control. The control is the result of a RFLP analysis of the pig prolactin receptor gene of a different pig where the polymorphism of the pig prolactin receptor gene is known. Similarly, the prolactin receptor genotype of a pig may be determined by obtaining a sample of its genomic DNA, conducting RFLP analysis of the prolactin receptor gene in the DNA, and comparing the results with a control. Again, the control is the result of RFLP analysis of the prolactin receptor gene of a different pig. The results genetically type the pig by specifying the polymorphism in its prolactin receptor genes. Finally, genetic differences among pigs can be detected by obtaining samples of the genomic DNA from at least two pigs, identifying the presence or absence of a polymorphism in the prolactin receptor gene, and comparing the results.

These assays are useful for identifying the genetic markers relating to litter size, as discussed above, for identifying other polymorphisms in the prolactin receptor gene that may be correlated with other characteristics, and for the general scientific analysis of pig genotypes and phenotypes.

The genetic markers, methods, and kits of the invention are also useful in a breeding program to improve litter size in a breed, line, or population of pigs. Continuous selection and breeding of sows that are at least heterozygous and preferably homozygous for a polymorphism associated with increased litter size would lead to a breed, line, or population having higher numbers of offspring in each litter of the females of this breed or line. Thus, the markers are selection tools.

It is to be understood that the application of the teachings of the present invention to a specific problem or environment will be within the capabilities of one having ordinary skill in the art in light of the teachings contained herein. The examples of the products and processes of the present invention appear in the following examples.

Example 1

Due to their high sequence homology and similarity in transcript processing, human (Boutin et al. 1989) and rabbit (Edery et al. 1989) cDNA sequences encoding the prolactin receptor were used to design degenerate primers overlapping the 3' coding and untranslated region. The primers amplified a fragment of approximately 500 base pairs in pig genomic DNA samples and human control. The forward primer 5'-TCA CAA GGT CAA C/TAA AGA TG-3' (SEQ ID NO:4) and the reverse primer 5'TGG/A AGA AAG/A AGG CAA G/ATG GT-3' (SEQ ID NO:5) were used in the following PCR conditions: 93° C. for 3 minutes, 6 cycles of 93° C. 30 seconds, 47° C. 2 minutes, 72° C. 3 minutes, 36 cycles of 93° C. 30 seconds, 53° C. 2 minutes, 72° C. 5 minutes, and a final 72° C. 5 minutes. The Taq polymerase was added last while samples were held at 80° C.

Fragments from two animals were purified and sequenced in forward and reverse directions. The pig sequence from the coding region was translated to amino acids and compared with known sequences. A database search reported the rabbit and human PRLR sequences as the two best matches, with 82% and 74% positives respectively. From the pig DNA sequence, primers (forward primer 5'-CCC AAA ACA GCA GGA GAA CG-3' (SEQ ID NO:1) and the reverse primer 5'-GGC AAG TGG TTG AAA ATG GA-3' (SEQ ID NO:2)) were designed to amplify a 457 base pair fragment (FIG. 1). The restriction endonucleases Taq1, Sau3a, PvuII, MspI, and AluI, were used to digest the amplified product and a polymorphism was found with AluI. Resolution of the bands was obtained using agarose gel electrophoresis (FIG. 2). The fragment sizes of the PCR-RFLP were approximately 124, 110, 79, 77, and 67 base pairs with the polymorphic site being located in the 110 base pair fragment. When the polymorphic cut site was present a 90 base pair fragment was produced. See FIG. 4 for the fragment patterns produced. The PiGMaP reference families (Archibald et al. 1995) were genotyped, with all available families being informative. The genotypes were analyzed for 2-point linkage using CriMap software (Green et al. 1990), with LOD scores greater than 3 being significant. The PRLR locus was closely linked to three markers which are mapped to pig chromosome 16 of the published PiGMaP linkage map. A multiple point analysis was also done to produce a best chromosome 16 map (FIG. 3) involving all linked markers.

Example 2

PCR TEST for Prolactin Receptor Genetic Marker

The PCR amplification test was optimized with the following parameters. Primers: forward primer 5'-CCCAAAACAGCAGGAGAACG-3' (SEQ ID NO:1) reverse primer 5'-GGCAAGTGGTTGAAAATGGA-3' (SEQ ID NO:2)

PCR conditions:

| Cocktail Mix | 25 µL reaction |
|---|---|
| 10X PCR buffer (Promega) | 2.5 µL |
| 25 mM MgCl$_2$ (Promega) | 2.0 µL |
| 10 mM dNTP's (Boehringer Mannheim) | 0.5 µL |
| 20 pmol/µL forward primer | 0.5 µL |
| 20 pmol/µL reverse primer | 0.5 µL |
| dd Sterile H$_2$O | 17.5 µL |
| 12.5 ng/µL DNA | 1.5 µL |
| Taq Polymerase (Promega) | 0.125 µL |

The first six reagents should be mixed and 18.5 uL of this pre-mix added to each reaction tube. Add the DNA next and then overlay with a drop of sterile mineral oil. Place the reaction tubes on the terminal cycler held at 80° C. Mix the Taq with the remaining cocktail and add 5 uL to the reaction tubes, making sure to submerge the tip beneath the oil.

Thermal Cycler Program:
1. 93° C. 3 minutes
2. 93° C. 30 seconds
3. 60° C. 1 minute
4. 72° C. 1 minute
5. Return to step 2 for 34 cycles
6. 72° C. 3 minutes
7. 4° C. hold 5 uL of the PCR product plus 2 uL of 6X loading dye should be placed on a 1 agarose gel to check. Run at 120 V for 30 minutes and stain with Ethidium Bromide.

AluI Digestion:

| Digestion Mix (per 20 µL PCR product) | Each |
|---|---|
| 10X NEBuffer 2 (New England Biolabs) | 2.5 µL |
| 8U/µL AluI (New England Biolabs) | 0.5 µL |
| dd Sterile H$_2$O | 2.0 µL |

Mix the reagents and add 5 uL to each tube. Incubate the samples at 37° C. overnight.

Gel Electrophoresis:

The fragments are separated by loading the digest product plus 5 uL 6X loading dye on a 6% NuSieve (FMC) agarose gel at 120 volts for 3 hours at room temperature. Stain gels with ethidium bromide. The fragment sizes of the PCR-RFLP are approximately 124, 110, 79, 77, and 67 base pairs with the polymorphic site being located in the 110 base pair fragment. When the polymorphic cut site is present a 90 base pair fragment is produced. Thus a heterozygote will have bands at 124,110,90,79,77 and 67. While homozygotes will have bands at 124,90,79,77 and 67 and 124,110,79, and 67 respectively.

Figure 4:
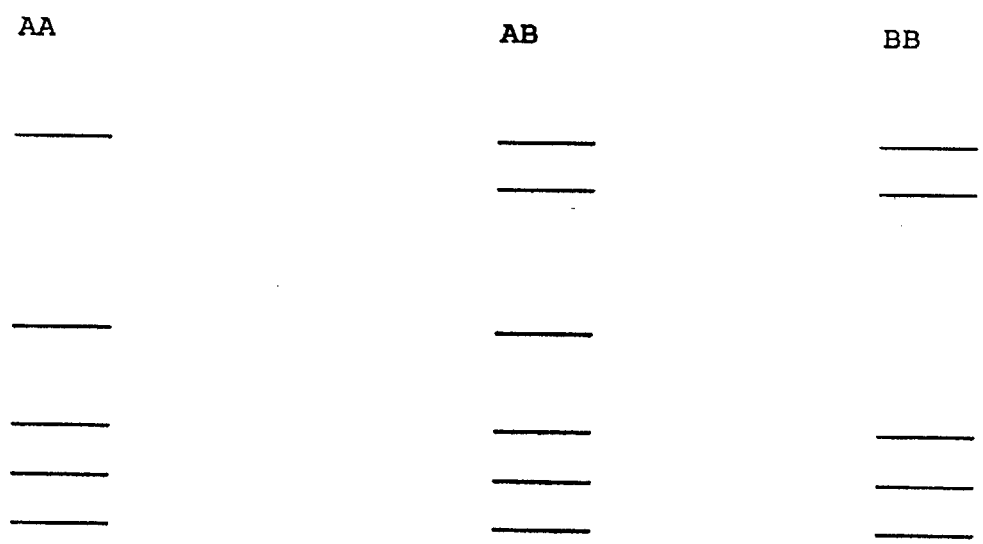
FIG. 4 is a diagram of the fragments obtained from the PCR test using PCR primers SEQ ID NOS: 1 and 2.

FIG. 4 is a diagram of the fragments obtained from the PCR test. (A is the allele with no AluI site, B is the allele having the AluI site).

Example 3

Association Of Genotype With Litter Size

The PCR test was run as detailed in Example 2 on several sows from Pig Improvement Company, (PIC). The animals used were PIC line 19 sows which farrowed within a six month period and gilts which were born during this period that would be kept as breeding stock. Blood or tissue samples were collected and shipped to the laboratory where the DNA was extracted and used in the PRLR PCR test. Females had one to three records used in the analysis. Estimated Breeding Value for Total Number Born (BV TNB) was estimated using a mixed linear model where each successive parity of the sow is treated as a repeated record. Only the first three parities of a sow were used. The model includes the covariate of age at farrowing nested within parity, fixed effects of parity, service type (natural or AI), farm-month farrowed, and random permanent environmental and animal effects. Current $h^2$ is assumed as 0.10 and repeatability as 0.21. Average Number Born (AV NB) was calculated by taking the arithmetic mean of total parities (1–3) for each female. Genotype comparisons were made for (BV TNB) and (AV NB) by averaging individual BV TNB and AV NB for each genotype. The results are seen in Table 1.

TABLE 1

L19 Means for PRLR genotypes

| BB Genotype | | |
|---|---|---|
| (n = 18) | BV TNB | AV NB |
| Mean | 0.2036 | 10.32 |
| Std Dev | 0.3984 | 1.746193 |
| Std Err | 0.0939 | 0.411838 |

| AB Genotype | | |
|---|---|---|
| (n = 75) | BV TNB | AV NB |
| Mean AB | 0.1203 | 9.66 |
| Std Dev AB | 0.5317 | 2.77238 |
| Std Err AB | 0.0622 | 0.320136 |

| AA Genotype | | |
|---|---|---|
| (n = 109) | BV TNB | AV NB |
| Mean AA | 0.0755 | 9.75 |
| Std Dev AA | 0.5757 | 2.513279 |
| Std Err AA | 0.0551 | 0.243064 |

Example 4

Summary of Analyses of Prolactin Receptor With a Large White Line and a Meishan Synthetic Line Below are tables summarizing analyses of the effect of litter size in a European Large White line and a recently created Meishan synthetic line. Models contained fixed effects of: herd-season, service type, prolactin receptor, parity (1,2,3+)
 covariable: ESR (estrogen receptor)
 random effect: sire Interactions among herd, ESR and prolactin receptor were tested for significance.

Main conclusions: Large White

Indications of a dominance effect.

The sample consisted of 400 sows with 1197 litter records. AA animals have a 0.66 pig/litter advantage in Number Born Alive (NBA) over the other two genotypes (p<0.05).

Meishan Synthetic

Significant dominance effect (over-dominance) -over all parities but mainly in first parity.

The sample consisted of 261 sows with 835 litter records. Additive and dominance effects of +0.17 and +0.67 respectively were identified with p<0.01. Effects on TNB showed the same trends as NBA for each of the populations. In addition, significant differences were not found for average Birth Weight. This is a potentially valuable observation as there is normally an inverse relationship between litter size and average birth weight. The prolactin receptor allele may therefore provide a method of increasing the birth weight of larger litters.

TABLE 2

Lsmeans across all parities for TNB, NBA and average birth weight (ABW)

|    | TNB   | NBA    | ABW   |
|----|-------|--------|-------|
| AA | 12.90 | 12.33a | 1.32  |
| AB | 12.48 | 11.67b | 1.33  |
| BB | 12.37 | 11.67b | 1.33  |
| a  | −0.27 | −0.33* | +0.01 |
| d  | −0.16 | −0.33+ | +0.01 |

Note:
columns with different letters significantly different (P < 0.05) +, P < 0.1; *, P < 0.05

TABLE 3

Lsmeans across all parities for TNB, NBA and average birth weight (ABW)

|    | TNB    | NBA     | ABW   |
|----|--------|---------|-------|
| AA | 14.90  | 13.10a  | 1.22  |
| AB | 14.79  | 13.93b  | 1.22  |
| BB | 14.42  | 13.43b  | 1.20  |
| a  | +0.17+ | +0.17** | −0.01 |
| d  | +0.54* | +0.67** | +0.01 |

Note:
columns with different letters significantly different (P < 0.05) +, P < 0.1; *, P < 0.05; **; P < 0.01

Example 5

Variation among different breeds

In addition, samples from seven breeds have been typed, including the U.S. breeds Chester White, Duroc, Hampshire, Landrace, and Yorkshire; the Chinese Meishan; and the European Large White (Table 2).

TABLE 4

| Breed | Genotype Frequencies | | | Allele Frequencies | |
|---|---|---|---|---|---|
|  | AA | AB | BB | A | B |
| Landrace n = 9 | .56 | .33 | .11 | .72 | .28 |
| Duroc n = 10 | .5 | .5 | 0 | .79 | .21 |
| Yorkshire n = 12 | 0 | .75 | .25 | .37 | .63 |
| Chester White n = 10 | .1 | .3 | .6 | .25 | .75 |
| Hampshire n = 11 | 0 | .09 | .91 | .05 | .95 |
| Meishan n = 9 | .33 | .44 | .22 | .56 | .44 |
| Large White n = 11 | .09 | .46 | .45 | .32 | .68 |

Some breed differences exist for gene frequencies at PRLR. The existence of a polymorphism located in the 3' region of the gene is interesting because PRLR alternative splicing is seen in this region of the gene in other species. The allele frequency differences among breeds suggest that one allele may have been selected for in some populations and against in others.

The following references are hereby incorporated in their entirety by reference: Archibald, A., Haley, C., Brown, J., Couperwhite, S., McQueen, H., Nicholson, D., Coppieters, W., Van de Weghe, A., Stratil, A., Wintero, A., Fredholm, M., Larsen, N., Nielsen, V., Milan, D., Woloszyn, N., Robic, A., Dalens, M., Riquet, J., Gellin, J., Caritez, J.C., Burgaud, G., Ollivier, L., Bidanel, J.P., Vaiman, M., Renard, C., Geldermann, H., Davoli, R., Ruyter, D., Verstege, E., Groenen, M., Davies, W., Hoyheim, B., Keiserud, A., Andersson, L., Ellegren, H., Johansson, M., Marklund, L., Miller, J., Anderson Dear, D., Signer, E., Jeffreys, A., Moran, C., Le Tissier, P., Muladno., Rothschild, M., Tuggle, C., Vaske, D., Helm, J., Liu, H.C., Rahman, A., Yu, T.P., Larson, R.G., Schmitz, C. (1995) The PiGMaP Consortium Linkage Map of the Pig (Sus scofa). Mamm. Genome 6, 157–175. Boutin, J., Edery, M., Shirota, M., Jolicoeur, C., LeSueur, L., Ali, S., Gould, D., Djiane, J., Kelly, P. (1989). Identification of cDNA Encoding a Long Form of Prolactin Receptor in Human Hepatoma and Breast Cancer Cells. Mol. Endocrinol. 3, 1455–1461. Edery, M., Jolicoeur, C., Levi-Meyrueis, C., Dusanter-Fourt, I., Petridou, B., Boutin, J., LeSueur, L., Kelly, P., Djiane, J. (1989). Identification and Sequence Analysis of a Second From a Prolactin Receptor by Molecular Cloning of Complementary DNA From Rabbit Mammary Gland. Proc. Natl. Acad. Sci. USA 86, 2112–2116. Green, P., Falls, K., Crooks S. (1990). Documentation for CRIMAP, version 2.4. Washington University School of Medicine, St. Louis. Jammes, H., Schirar, A., Djiane, J. (1985) Differential Patterns in Luteal Prolactin and LH Receptors During Pregnancy in Sows and Ewes. J. Reprod. Fertil. 73, 27–35. Kelly, P., Djiane, J., Postel-Vinay, M., Edery, M. (1991). The Prolactin/Growth Hormone Receptor Family. Endocrin. Rev. 12.235–251. Lebrun, J., Ali, S., Groffin, V., Ullrich, A., Kelly, P. (1995). A Single Phosphotyrosine Residue of the Prolactin Receptor is Responsible for Activation of Gene Transcription. Proc. Natl. Acad. Sci. USA 92, 4031–4035. LeSueur, L., Edery, M., Ali, S., Paly, J., Kelly, P. (1991). Comparison of Long and Short Forms of the Prolactin Receptor on Prolactin-Induced Milk Protein Gene Transcription. Proc. Natl. Acad. Sci. USA 88, 824–828. Rothschild, M., Jacobson, C., Vaske, D., Tuggle, C., Wang, L., Short, T., Eckardt, G., Sasaki, S., Vincent, A., McLaren, D., Southwood, O., van der Steen, H., Mileham, A., Plastow, G. (1996). The Estrogen Receptor Locus is Associated With a Major Gene Influencing Litter Size in Pigs. Proc. Natl. Acad. Sci. 93, 201–205. Rui, H., Djeu, J., Evans, G., Kelly, P., Farrar, W. (1992). Prolactin Receptor Triggering. J. Biol. Chem. 267, 24076–24081.

Yuan, W., Lucy, M. (1996). Effects of Growth Hormone, Prolactin, Insulin-Like Growth Factors, and Gonadotropins on Progesterone Secretion by Porcine Luteal Cells. J. Anim. Sci. 74, 866–872.

What is claimed is:

1. A primer for assaying for the presence of a polymorphic AluI site in the pig prolactin receptor gene wherein said primer comprises a sequence selected from the group consisting of SEQ ID NO: 1, SEQ ID NO:2, SEQ ID NO:4 and SEQ ID NO:5.

2. A DNA sequence from the pig prolactin receptor gene 3' translated and nontranslated region, said sequence consisting of SEQ ID NO:3.

3. A method of screening pigs to determine those more likely to produce larger litters comprising: obtaining a DNA sample from a pig; and assaying for the presence of a genotype characterized by a polymorphic Alu I site in the 3' region of the pig prolactin receptor gene, said genotype being one which is associated with increased litter size.

* * * * *

```
                            SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CCCAAAACAG CAGGAGAACG                                              20

(2) INFORMATION FOR SEQ ID NO:2:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

GGCAAGTGGT TGAAAATGGA                                              20

(2) INFORMATION FOR SEQ ID NO:3:

(i) SEQUENCE CHARACTERISTICS:
             (A) LENGTH: 492 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (ix) FEATURE:
             (A) NAME/KEY: allele
             (B) LOCATION: replace(240..241, "g")

(ix) FEATURE:
             (A) NAME/KEY: unsure
             (B) LOCATION: replace(440..449, "ccaaaactac")

(xi) SEQUENCE DESCRIPTION: SEQ ID NO:3:

AAGTCAACAA AGATGGAGCA CTGGCGTTGC TCCCAAAACA GCAGGAGAAC GGCGACCGGC        60

CGGAGAAGGC TGGCGCCCCT GAAACCAGCA AGGAATACGC CCAGGTGTCC CGGGTGATGG       120
```

```
ATAACCACAT CCTGGTGTTA GTGCAGGATC CGCGAGCTCG AAACGTGGCT CCGTTTGAAG      180

AACCAACCAA GGAGACCCCG CCATCCCGGC CGCAGAATCC AGCTGCGAAA GACCTGGCCA      240

GCTTCACCAC GGCCCCGGGC CACTGCAGAC ACCCGCTGGG TGGGCTGGAT TACCTCGATC      300

CCGCAGGCTT TATGCACTCC TTTCAGTGAG AGCTTGGTTC ATGGGATGAT GGGTTACAAG      360

GTGGGGTTTT TTTCAGGTCG CACTACGTGA AATGCACTCT ACCAGAGAAA GCTCGAAAAT      420

GGGGTTAGAA TGACACTACC CAGACTCACA GTTCACTCCT CTTCATGCTC CATTTTCAAC      480

CACTTGCCTC TT                                                         492
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
TCACAAGGTC AAYAAAGATG                                                  20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

```
TGRAGAAARA GGCAARTGGT                                                  20
```